United States Patent [19]

Sollevi

[11] Patent Number: 5,449,665

[45] Date of Patent: Sep. 12, 1995

[54] CONTINUOUS INTRAVENOUS INFUSION OF ADENOSINE TO HUMAN PATIENTS UNDERGOING PERCUTANEOUS TRANSLUMINAL ANGIOPLASTY

[75] Inventor: Alf Sollevi, Bromma, Sweden

[73] Assignee: Item Development Aktiebolag, Stocksund, Sweden

[21] Appl. No.: 167,745

[22] Filed: Dec. 15, 1993

Related U.S. Application Data

[60] Division of Ser. No. 31,666, Mar. 15, 1993, which is a division of Ser. No. 821,395, Jan. 14, 1992, Pat. No. 5,231,086, which is a continuation of Ser. No. 630,413, Dec. 19, 1990, Pat. No. 5,104,859, which is a continuation of Ser. No. 138,306, Dec. 28, 1987, abandoned, which is a continuation-in-part of Ser. No. 30,245, Mar. 24, 1987, abandoned, which is a continuation-in-part of Ser. No. 779,516, Sep. 24, 1985, abandoned.

[51] Int. Cl.$^6$ ............................................. A61K 31/70
[52] U.S. Cl. ...................... 514/46; 536/27.6
[58] Field of Search ............... 514/46; 604/95; 424/94.64

[56] References Cited

U.S. PATENT DOCUMENTS

| | | | |
|---|---|---|---|
| 4,673,563 | 6/1987 | Berne et al. | 424/9 |
| 5,104,859 | 4/1992 | Sollevi | 514/46 |
| 5,231,086 | 7/1993 | Sollevi | 514/46 |

OTHER PUBLICATIONS

Fukunaga et al. (I), "Hypotensive Effects of Adenosine and Adenosine Triphosphate Compared with Sodium Nitroprusside", *Anesthesia and Analgesia*, 61, 273–278 (1982).
Fukunaga et al. (II), "ATP-Induced Hypotensive Anesthesia During Surgery," *Anesthesiology*, 57(3), A65 (1982).
Masters et al., "Platelet Anti-aggregating and Hemodynamics Effects of Adenosine and Prostaglandin $E_1$", *Thorac. Cardiovasc. Surgeon*, 30, 14–20 (1982).
Kassel et al., "Cerebral and Systemic Circulatory Effects of Arterial Hypotension Induced by Adenosine," *J. Neurosurg.* 58, 69–76 (1983).
Sollevi et al., "Relationship Between Arterial and Venous Adenosine Levels and Vasodilation During ATP- and Adenosine-Infusion in Dogs," *Acta Physiol. Scand.*, 120, 171–176 (1984).
Olsson et al., "Coronary Vasodilation of Adenosine in the Conscious Dog," *Circulation Research*, 45(4), 468–478 (1979).
Drury et al., "The Physiological Activity of Adenine Compounds with Especial Reference to Their Action Upon the Mammalian Heart," *J. Physiology* (Cambridge), 68, 213–237 (1929).

*Primary Examiner*—Douglas W. Robinson
*Assistant Examiner*—L. Eric Crane
*Attorney, Agent, or Firm*—White & Case

[57] ABSTRACT

This invention is concerned with the use of adenosine as an agent for the treatment of human beings. More particularly, this invention is concerned with the administration of adenosine to human patients by continuous intravenous infusion for, inter alia, control of blood pressure, use as a selective vasodilator, decreasing pulmonary vascular resistance, treating acute pulmonary hypertension in conjunction with idiopathic respiratory distress syndrome, in diagnosing pulmonary hypertension in conjunction with cardiac septum defects, in percutaneous transluminal angioplasty (PTCA), in coronary thrombolysis (CTL) and in radionucleide scintography.

3 Claims, No Drawings

CONTINUOUS INTRAVENOUS INFUSION OF ADENOSINE TO HUMAN PATIENTS UNDERGOING PERCUTANEOUS TRANSLUMINAL ANGIOPLASTY

This application is a divisional of application Ser. No. 08/031,666, filed Mar. 15, 1993, which is divisional of application Ser, No. 07/821,395, filed Jan. 14, 1992, now U.S. Pat. No. 5,231,086, which is a continuation of application Ser. No. 07/630,413, filed Dec. 19, 1990, now U.S. Pat. No. 5,104,859, which is a continuation of application Ser. No. 138,306, filed Dec. 28, 1987, now abandoned, which is a continuation-in-part of application Ser. No. 030,245, filed Mar. 24, 1987, now abandoned, which is a continuation-in-part of application Ser. No. 779,516, filed Sep. 24, 1985, now abandoned.

This invention is concerned with the use of adenosine as an agent for the treatment of human beings. More particularly, this invention is concerned with the administration of adenosine to human patients by continuous intravenous infusion for, inter alia, control of blood pressure, use as a selective vasodilator, decreasing pulmonary vascular resistance, treating acute pulmonary hypertension, treating pulmonary hypertension in conjunction with idiopathic respiratory distress syndrome, and in diagnosing pulmonary hypertension in conjunction with cardiac septum defects.

Adenosine is a naturally occurring nucleoside composed of the purine, adenine, and the sugar, D-ribose. Normal basal plasma levels of adenosine are from about 0.1 to about 0.2 $\mu$mol per liter. In addition, it is commonly present in the body in the form of adenosine monophosphate (AMP), adenosine diphosphate (ADP) and adenosine triphosphate (ATP). Adenosine has been reported to have a variety of biological effects, depending on whether the adenosine is endogenous or exogenously administered, including sedative and anti-epileptic effects on the central nervous system and inhibitory effects on respiration, cardio-vascular effects, including prolongation of atrio-ventricular conduction time and impulse formation in the sinus node, vasodilation, antiaggregatory effect, decreased release of free fatty acids, anti-secretory effect in the stomach, and anti-diuretic effect.

As a general rule, however, adenosine and its biological effects have been largely of physiological interest. To the extent adenosine was of interest as a pharmaceutical product, that interest has centered primarily on its phosphate derivative, which now is known to be rapidly metabolized to yield adenosine and phosphate in the circulation. See Sollevi et al., Acta. Physiol. Scand. 120:171–6 (1984). However, phosphate may cause undesired side effects. For example, high levels of phosphate may cause arrhythmias secondary to chelation of magnesium and calcium. (See Dedrick, et al., Anesthesiology, 57:3A, 66 (1982)).

Furthermore, adenosine is known to produce heart block through blockage of the atrioventricular (A-V) node. As a consequence, methylxanthines such as theophylline have been proposed by Berne, et al., in U.S. Pat. No. 4,364,922 for use in preventing heart block caused by adenosine, in particular adenosine released as a consequence of cardiac ischemia or hypoxia.

In addition, it has been proposed to take advantage of adenosine's ability to block atrioventricular conductance by using it to treat tachyarrhythmias. For such use, adenosine is administered as an injectable intravenous bolus containing from about 37.5 micrograms/kg up to about/450 micrograms/kg of adenosine. In such a use, the adenosine has little detectable vasodilating action. Adenosine has a very short plasma half-life, of the order of 10–20 seconds (see, Fredholm and Sollevi, J. Physiol., 313:351–62 (1981)), and thus the concentration of injected adenosine is rapidly reduced to normal serum levels (about 0.15 $\mu$mol per liter). The transitory presence of the injected adenosine precludes all but the most transitory vasodilation.

Accordingly, for adenosine to be of practical value for use as a vasodilator, it must be administered continuously to maintain plasma levels sufficiently high to achieve vasodilation. The problem, however, is that such continuous administration could lead to undesired side effects, such as the above-noted heart blockage.

It also should be noted that compounds commonly used as vasodilators, such as sodium nitroprusside, nitroglycerine, isoflurane, hydralazine, prazosin and the like, have various side effects. For example, sodium nitroprusside has the drawbacks of tachyphylaxis and rebound hypertension, apparently caused by autogenous generation of angiotensin to counteract the hypotensive effect of the nitroprusside. As a consequence, the dosage of nitroprusside must be progressively increased with continued use to overcome the hypertensive effect of angiotensin, and there is a risk of rebound due to the presence of residual excess angiotensin. Nitroglycerine and prazosin suffer from the drawbacks of slow onset and unpredictable action. Isoflurane and sodium nitroprusside both have a tendency to reduce cardiac blood flow, while nitroprusside, hydralazine and prazosin increase heart rate.

Accordingly, there remains a need for a vasodilator suitable for administration by continuous intravenous infusion.

The present invention is based upon the discovery that adenosine can be administered to human patients under conditions such that significant vasodilation is achieved without the occurrence of significant heart blockage. It is based on the further discovery that adenosine has a unique, and heretofore unappreciated, activity profile in humans which differs significantly from the profiles of heretofore commonly used vasodilators. As a consequence of this discovery, it has been discovered that adenosine may be employed for the treatment of a variety of conditions by continuous intravenous infusion techniques. In particular, and as will be illustrated in greater detail below, adenosine has been found to have the following characteristics:

1. It has selective vasodilation activity, in that its effect is limited to a cardiac after-load effect. That is, its activity is limited to dilation of arteries and it has little or no effect on cardiac pre-load, i.e. as a dilator of veins.
2. Although adenosine has significant action in blocking atrio-ventricular (A-V) conductance by bolus injection, it can be administered by continuous infusion and have significant useful vasodilating action at dosages below those at which it has significant A-V activity.
3. Adenosine has significant hypotensive activity without the occurrence of significant tachyphylaxis, apparently because adenosine blocks the renin-angiotensin system of the kidney, thus preventing hypertension due to the formation of angiotensin in response to hypotension.

4. Adenosine's effect is readily controlled because it is active at relatively small doses and because of its short plasma half-life (10–20 seconds). In addition, its activity quickly ceases when adenosine administration is terminated.
5. Adenosine is capable of significantly increasing cardiac output without significantly increasing cardiac work.
6. Adenosine, in the amounts used in accordance with the invention, is essentially non-toxic. It is rapidly taken up by the body to form-ATP, and upon degradation its metabolites are present at or below levels normally resulting from physical exercise.

The foregoing activity profile permits continuous infusion of adenosine for controlled hypotension during surgery, for control of various forms of hypertensive crisis, to improve coronary circulation during surgery in patients with ischemic heart disease, for reducing the incidence of coronary graft occlusion by increasing graft flow following coronary bypass surgery, and for reducing platelet loss during cardiac bypass surgery. It has also been found that adenosine may be used for decreasing pulmonary vascular resistance, for treating acute pulmonary hypertension, for treating acute pulmonary hypertension in conjunction with idiopathic respiratory distress syndrome (IRDS) and for diagnosing the operability of the pulmonary vasculature in patients with pulmonary hypertension in conjunction with cardiac septum defects. Adenosine also is useful in inhibiting clot formation during percutaneous transluminal coronary angioplasty (PTCA) and coronary thrombolysis (CTL), as well as an aid in visualizing miocardial irrigation for radionucleotide scintigraphy.

In accordance with this invention, adenosine may be administered to human patients by continuous intravenous infusion to provide significant vasodilation and without significant heart blockage under two conditions. First, the heart blocking action of adenosine is not detected during anesthesia when the rate of administration is 0.35 milligrams of adenosine per kilogram of body weight per minute or less. Second, the heart blocking action of adenosine is not detected, even in conscious patients, at rates of administration of about 0.10 milligram of adenosine per kilogram of body weight per minute or less.

For purposes of this invention, adenosine can be administered to the patient in any pharmaceutically acceptable form suitable for use in continuous, intravenous infusion. A preferred form is an aqueous solution of adenosine, and more preferably adenosine in isotonic saline. The concentration of adenosine in the solution is not narrowly critical, although concentrations of at least about 5 millimol (or about 1.5 milligrams) per milliliter of solution are desired to avoid the need for excessive infusion rates to achieve desired serum levels. When administering adenosine to small children, however it is possible to use concentrations as low as about 0.1 mg/ml. The concentration may be as high as the solubility limit of adenosine (about 20 millimols per liter or 5.5 to 6 milligrams per milliliter), if desired.

When used for continuous infusion in accordance with this invention, the unit dosage form typically has a volume of at least 250 milliliters, and preferably in the range of 250 to 500 milliliters, to provide an adequate supply of adenosine. Consequently, the unit dosage form generally will contain from about 0.4 to about 3 grams of adenosine. In small children, the unit dose will, of course, be correspondingly smaller than it is for adults.

The adenosine solution should be sterile and free from fungi and bacteria. Such solutions have been found to be stable at room temperature for at least two years.

Such solutions are prepared by mixing adenosine with the aqueous carrier, e.g. water or an isotonic solution, and other desired ingredients, to achieve a solution having the desired concentration, and thereafter sterilizing the solution.

Continuous infusion can be performed using any technique known to the art. Because adenosine has such a short plasma half-life and it is active at relatively low concentrations, it is desired that the method be one which minimizes or avoids fluctuations of serum adenosine levels. Accordingly use of high precision roller pumps is preferred.

As is noted above, the present invention has numerous specific applications, depending upon adenosine dosage levels and whether or not adenosine is administered to anesthesized or conscious patients. The first general category of applications is that in which adenosine is continuously administered to a patient undergoing surgery under general anesthesia at doses that do not induce heart block. Specific applications include controlled hypotension during surgery, in particular dissection and clipping of cerebral arterial aneurysms; control of hypertension crisis during surgery, for example due to release of catecholamines in the course of pheochomocytoma surgery; and improved coronary circulation and after-load reduction during abdominal aortic aneurysm surgery, especially in patients with ischemic heart disease. For such uses, dosage rates of the order of 0.05 to about 0.3 milligrams per kilogram of body weight per minute are effective amounts.

The second general category of continuous adenosine infusion applications is that in which adenosine is administered to conscious patients, also at levels below which adenosine exhibits significant heart blocking action. These levels are typically achieved at administration rates of 0.05 milligram of adenosine per kilogram per minute or less. Specific examples of conditions which may be treated with adenosine in conscious patients include prevention of occlusion of cardiac bypass grafts following bypass surgery, increased cardiac output in patients with low cardiac output, and use of adenosine as an adjunct to dopamine treatment for shock.

Blood levels of adenosine which result from an administration rate of about 10–30 micrograms per kilogram of body weight per minute (0.010–0.030 mg. per kg. per minute) can be used in a number of additional ways, e.g., to decrease pulmonary vascular resistance, to treat acute pulmonary hypertension and acute pulmonary hypertension in conjunction with idiopathic respiratory distress syndrome (IRDS), and to diagnose pulmonary hypertension in conjunction with cardiac septum defects.

The following examples illustrate in greater detail specific applications of continuous intravenous infusion of adenosine in accordance with this invention.

EXAMPLE I

Controlled Hypotension During Anesthesia

It is frequently desired to reduce the blood pressure of patients during surgery. For example, in the case of dissection and clipping of cerebral arterial aneurysms, controlled hypotension is desired to reduce the aneurysm wall tension in order to minimize the risk of rupture and bleeding. Controlled hypotension is also used to reduce bleeding during other forms of surgery.

Prior to this invention, vasodilators, such as sodium nitroprusside and nitroglycerine, were used for this purpose, but both have drawbacks. For example, sodium nitroprusside suffers from tachyphylaxis, or the need to increase the dose of nitroprusside with time due to the release of angiotensin. In addition, rebound hypertension also has been observed following use of nitroprusside. Nitroglycerine is characterized by slow onset of action and unpredictable action.

Adenosine has been found to be a remarkably effective agent for inducing controlled hypotension during surgery. Adenosine, when administered in effective amounts, has a very rapid hypotensive effect which can be rapidly terminated due to its short half-life. Moreover, adenosine does not cause tachyphylaxis, apparently because it blocks the renin-angiotensin system of the kidney, thereby preventing formation of angiotensin which tends to counteract the hypotension. For the same reason, rebound hypertension is avoided after discontinuation of infusion.

For this indication, adenosine typically is administered intravenously via the left basilic vein or via a central vein in an amount (or at a rate) sufficient to achieve the desired hypotensive effect. It has been found that lowering of mean arterial blood pressure to as low as 40 millimeters of mercury, as measured by a cannula in the left radial artery, is readily achieved without significant side effects. In particular, so long as the patient is under anesthesia, no blockage of atrio-ventricular conductance is observed.

The actual plasma levels of adenosine employed for controlled hypotension will vary, depending upon such factors as the particular patient, the age of the patient and the desired degree of hypotension. As a general rule, however, a reduction of mean arterial blood pressure to 40 to 50 mm Hg is achieved by adminstration of adenosine at a rate of from about 0.2 to about 0.35 milligrams of adenosine per kilogram of body weight per minute. The amount of adenosine required to achieve a given degree of hypotension can be reduced if adenosine uptake inhibitors, such as dipyridamole, are also administered to the patient. The possibility that adenosine might be useful for inducing contolled hypotension in humans was suggested by Kassell et al., J. Neurosurg., 58: 69–76 (1983), based upon tests in dogs. However, this study was performed during the administration of dipyridamole, another vasodilator that potentiates the effect of adenosine by inhibiting cellular uptake of adenosine. The dose of dipyridamole (1 mg/kg) was high, and it in fact induced a 20% reduction of the mean arterial blood pressure. The hypotensive effect of adenosine was then studied upon this hypotensive dose of dipyridamole. It was reported that hypotension to a mean arterial pressure of 40 mm/Hg could be induced and maintained with an infusion of 0.4 gram of adenosine per 100 milliliters of normal saline, at a dose of 50 µg/kg/minute. When dipyridamole was excluded in a pilot study, as much as 5–10 mg/kg/minute was required for the induction of hypotension, thereby creating an excessive fluid load. Kassel et al. noted that induction of hypotension in dogs is difficult, and speculated that "adenosine alone, without the potentiating effects of dipyrimadole, may be sufficient to produce hypotension in man without excessive volumes of fluid". As noted above, effective induction of hypotension in man is achieved at adenosine dose levels of only 0.2 to 0.35 mg/kg/minute, or 30 to 50 times lower levels than effective levels in the dog. Such low rates are hardly predictable from the information of Kassel et al.

In a study intended to demonstrate use of continuous infusion of adenosine to effect controlled hypotension in man, ten patients with no known history of cardiopulmonary diseases (seven men and three women, ages 35–58 years), scheduled for intracerebral aneurysm surgery, were selected.

One hour before the operation the patients were premedicated orally with diazepam (10–20 mg.) Atropine (0.5 mg) and droperidol (0.1 mg. per kg.) were given intravenously before induction of anesthesia. Induction was started with thiopental (5 mg. per kg) followed by phenoperidine (1–2 mg), a synthetic opiate with pharmacodymanics resembling fentanyl but with a lounger duration of action and 1/10 of its analgesic potency.

Pancuronium bromide (0.1 mg per kg) was given to facilitate endotracheal intubation. Anesthesia was maintained by supplementary doses of phenoperidine and droperidol, as required. The total dose of droperidol did not exceed 0.2 mg. per kg. and was administered within the first 2 hours of anesthesia. Phenoperidine was supplemented regularly to prevent the blood pressure from exceeding the preanesthetic level (approx. 1 mg/30–60 min). Controlled hyperventilation was employed with a humidified gas mixture of 60% $N_2O$ in oxygen to maintain $PaCO_2$ values at approximately 30 mmHg ($\pm 1.5$/SEM). Mannitol (1–1.5 g. per kg) was given routinely at the start of the operation (e.g., 1–2 hours prior to the controlled hypotension). The patients were operated on in the horizontal supine position.

A 1.2-mm plastic cannula was introduced into the left radial artery to monitor systemic arterial blood pressure (MABP) and collect arterial blood. A balloon-tipped, flow-directed, quadruple lumen Swan-Ganz catheter (Model 93A-831–7.5 F, VIP) was inserted percutaneously via the left basilic vein, and its correct position in the pulmonary artery was determined by pressure tracings. The catheter was used for the monitoring of mean right atrial pressure (RAP), mean pulmonary artery pressure (PAP), and mean pulmonary capillary wedge pressure (PCWP) for the determination of cardiac output and collection of mixed venous blood and lot the infusion of adenosine. Another plastic cannula was introduced percutaneously, in a retrograde direction, into the right jugular bulb for the collection of blood. The correct position was verified by x-ray.

The ECG was monitored with a standard chest (V5) lead. Heart rate was determined from the R-R interval. Blood pressures were measured by transducers placed at the midthoracic level. Cardiac output (QT) was determined in triplicate according to the thermodilution technique with a cardiac output computer (Edwards Lab, model 9510). Isotonic glucose, 10 ml at 1° C., was used as a thermal indicator. The ECG, heart rate, blood pressures, and thermodilution curves were recorded on a Grass ® polygraph.

Blood gases were measured with appropriate electrodes for pH, $PCO_2$, and $PO_2$ (Radiometer, Copenhagen). The hemoglobin concentration was determined spectrophotometrically. Samples for the determination of adenosine and its metabolites were collected as described by Sollevi et al., Acta Physiol. Scand., 120: 171–76 (1984). Adenosine and inosine were purified and analyzed by HPLC as described by Fredholm and Sollevi., J. Physiol. (London), 313: 351–67 (1981). Hypoxanthine, xanthine, and uric acid were analyzed by HPLC according to the method of Schweinsberg and Loo., J. Chromatogr., 181: 103–7 (1980). Arterial levels of dipyridamole were determined by HPLC. J. Chromatogr., 162: 98–103 (1979). Blood lactate was measured according to Tfelt-Hansen and Siggard-Andersen. Scand. Clin. Lab. Invest., 27: 15–19 (1971).

Measurements and blood samplings were performed immediately before hypotension, as late as possible during hypotension (1–5 min before terminating the infusion) and approximately 30 min after the hypotensive period.

Dipyridamole (5 mg. per ml) was infused iv (0.3–0.4 mg. per kg. over a period of 5–10 min) approximately 20 minutes prior to the induction of controlled hypotension. This dose of dipyridamole produced clinically relevant drug levels in the plasma (1.2±0.3 $\mu$M, SEM) during the hypotensive periods. (See Pedersen, J. Chromatogr., 162: 98–103 (1979).

Adenosine (5 mM, 1.34 mg. per ml in isotonic saline) was administered by continuous infusion (Critikon roller pump, 2102A, superior vena cava) for 12–71 minutes ($\bar{x}=33\pm3$ SEM) at a rate of 0.01–0.32 mg. per kg per min ($\bar{x}=0.14\pm0.04$ SEM, corresponding to 8.0±2.7 mg. per min). The infusion was started at a rate of 0.01 mg. per kg. per minute, which was doubled at 15 second intervals until the desired MABP level of 40–50 mmHg was reached. The corresponding volume of infused adenosine solution ranged from 0.5 to 17 ml. per min ($\bar{x}=6\pm2$ SEM). The mean hypotensive period was 32±8 min. The total adenosine dose did not exceed 1.5 grams. Serum creatinine was determined before and on two consecutive days after operation. The standard ECG was recorded the day before and the day after operation.

Systemic vascular resistance (SVR) was derived from the formula $$SVR \text{ (mmHg. per liter min)} = \frac{MABP - RAP}{QT}$$

and pulmonary vascular resistance (PVR) from the formula $$PVR = \frac{PAP - PCWP}{QT}.$$

Oxygen content was derived from the formula $SO_2^* \times 1.34 \times Hb + PO_2 \times 0.03$. Foex et al., Br. J. Anesth., 42: 803–4 (1970). The arteriovenous oxygen content difference ($AVDO_2$) was determined and used to calculate total oxygen consumption ($VO_2$) as the product of $AVDO_2$ and QT.

*$SO_2$ = Oxygen saturation.

The results of this work are summarized in Tables I–IV, in which data are presented as means±SEM. The statistical significance (control 1 vs. adenosine and control 1 vs. control 2) was determined by Student's t test for paired data. A P value of <0.05 was regarded as significant.

The purine levels of nine of the patients were determined prior to, during and after adenosine-induced controlled hypotension. The results are summarized in Table I.

TABLE I

Purine Levels ($\mu$M) in Arterial Plasma Before, During, and After Adenosine-induced Controlled Hypotension in Nine Patients

| | Control 1 | Hypotension | After Hypotension | |
|---|---|---|---|---|
| | | | 3–9 Min | 20–40 Min |
| Adenosine | 0.15 ± 0.02 (9) | 2.45 ± 0.65 (9) | 0.24 ± 0.06 (6) | 0.19 ± 0.03 (7) |
| Inosine | 0.04 ± 0.01 (8) | 3.01 ± 1.48 (8) | 0.69 ± 0.26 (5) | 0.29 ± 0.15 (7) |
| Hypoxanthine | 1.94 ± 0.55 (9) | 6.28 ± 2.33 (9) | — | 3.25 ± 1.00 (8) |
| Xanthine | 5.93 ± 2.04 (7) | 6.10 ± 1.67 (7) | — | 5.49 ± 1.58 (7) |
| Uric Acid | 185.2 ± 14.2 (19) | 198.1 ± 22.7 (9) | — | 199.5 ± 28.8 (8) |

*P < 0.01
**P < 0.05, denotes significantly different from the control 1 levels.
Number of observation in parentheses.

As is evident from Table I, adenosine is present in the $10^{-7}$M range during basal conditions. Continuous infusion of adenosine increased the arterial adenosine level to 2.45±0.65 $\mu$M. The adenosine metabolites inosine and hypoxanthine were increased during the infusion, whereas xanthine and uric acid levels were unaffected. Once the desired blood pressure level was reached, the infusion rate could be kept constant throughout the hypotensive period. After termination of the infusion, the arterial adenosine levels returned to control values within 3–9 min. Inosine was eliminated more slowly from tile circulation and remained slightly above basal levels 20–40 minutes after the infusion.

The central hemodynamic variables were measured in all 10 patients before, during and 30 minutes after controlled hypotension and are summarized in Table II.

TABLE II

Central Hemodynamic Variables Before, During and 30 Min After Adenosine-induced Controlled Hypotension in Ten Patients.

| | Control 1 | Adenosine | Control 2 |
|---|---|---|---|
| Systolic blood pressure (mmHg) | 115 ± 6 | 78 ± 6* | 130 ± 7** |
| Diastolic blood pressure (mmHg) | 61 ± 3 | 34 ± 2* | 71 ± 3** |
| Mean arterial blood pressure (mmHg) | 82 ± 3 | 46 ± 2* | 91 ± 4** |
| Right atrial pressure (mmHg) | 6.8 ± 1.1 | 7.2 ± 0.7 | 5.6 ± 0.8 |
| Pulmonary artery pressure (mmHg) | 14.4 ± 1.0 | 16.5 ± 0.9 | 14.7 ± 1.4 |

TABLE II-continued

Central Hemodynamic Variables Before, During and 30 Min After Adenosine-induced Controlled Hypotension in Ten Patients.

|  | Control 1 | Adenosine | Control 2 |
|---|---|---|---|
| Pulmonary capillary wedge pressure (mmHg) | 9.6 ± 1.1 | 11.0 ± 1.0 | 9.9 ± 1.4 |
| Heart rate (beats per min) | 54 ± 2 | 63 ± 3* | 58 ± 3 |
| Cardiac output (liters per min) | 4.93 ± 0.51 | 6.86 ± 0.71* | 5.17 ± 0.54 |
| Systemic vascular resistance (mmHg per min) | 16.65 ± 1.95 | 6.22 ± 0.60* | 17.70 ± 1.72 |
| Pulmonary vascular resistance (mmHg per liter min) | 0.97 ± 0.15 | 0.82 ± 0.08 | 0.97 ± 0.15 |

*$p < 0.01$
**$p < 0.05$, denotes significantly different from control 1.

The infusion of dipyridamole decreased MABP by approximately 10 mmHg in five of the patients. At the start of the adenosine infusion, MABP was not significantly different from the predipyridamole level (82±3 vs. 86±3 mmHg) as shown in Table II. Adenosine induced a decrease in MABP to 46 mmHg (43±3%) within 1–2 minutes.

The decrease in MABP was caused by a parallel decrease in both systolic and diastolic pressure. The MABP was stable throughout the hypotensive period. Cardiac output increased from 4.9 to 6.9 l per minute (44±9%) in parallel with a small increase in heart rate of 9±2 beats per minute. The SVR decreased from 16.7 to 6.2 mmHg per liter a minute, corresponding to a decrease of 61±3%, whereas PVR was unchanged. RAP, PAP, and PCWP were not influenced by adenosine.

After discontinuation of the infusion, MABP was restored within 1–5 minutes. Rebound hypertension did not occur, although the MABP was persistently approximately 10 mmHg higher after hypotension than during the control period. However, the posthypotensive MABP was not significantly higher than the MABP before administration of dipyridamole. Heart rate, QT, and SVR returned rapidly to control levels concurrently with the restoration of MABP.

Oxygen contents, consumptions and lactate concentrations in nine patients before, during and 30 minutes after controlled hypotension are summarized in Table III.

TABLE III

Total Arteriovenous Oxygen Content Difference (AVDTO2), Jugular Arteriovenous Oxygen Content Difference (AVDjO2), Total Oxygen Consumption (V$_T$O2), Arterial Oxygen Tension (PaO2), Arterial Lactate Concentration (La) and Jugular Arteriovenous Lactate Content Differences (AVDjLa) before, during, and after Adenosine-induced Hypotension in Nine Patients.

|  | Control 1 | Adenosine | Control 2 |
|---|---|---|---|
| AVD$_T$O$_2$ (ml per liter) | 46.3 ± 2.3 | 29.3 ± 2.5* | 46.8 ± 3.2 |
| AVD$_j$O$_2$ (ml. per liter) | 85.2 ± 10.5 | 58.1 ± 14.1** | 74.9 ± 7.7 |
| V$_T$O$_2$ (ml per mm.) | 220 ± 15 | 193 ± 16** | 235 ± 16 |
| Pa$_{O2}$ (mmHg) | 111.0 ± 9.8 | 97.5 ± 9.0 | 93.0 ± 5.2 |
| La (mmol per liter) | 1.46 ± 0.17 | 1.73 ± 0.20 | 1.82 ± 0.20** |
| AVD$_j$La (mmol per liter) | 0.02 ± 0.04 | −0.05 ± 0.05 | −0.06 ± 0.04 |

*$P < 0.01$
**$P < 0.05$, denotes significantly different from control 1.

From Table III, it can be seen that arterial oxygen tension remained unchanged during adenosine-induced hypotension. VO$_2$ was decreased by 13±4%, with a decrease in AVDO$_2$ of 37±5%. The arterial lactate concentration was not affected by hypotension. The cerebral AVDO$_2$ decreased similarly by 37±13%, while the arterio-jugular lactate content difference was unaltered.

After the hypotensive period, the metabolic variables returned to the control levels, except for a minor increase in the arterial lactate concentration.

The ECG the day after the operation was unchanged. The mean serum creatinine level was 83±4 μM before operation and 70±3 and 71±4 μM on the first 2 postoperative days.

Adenosine infusion rate was constant during the hypotension, which suggests the absence of tachyphylaxis.

Subsequent to the tests described above, a 20 mM solution of adenosine in isotonic saline was administered to 50 surgical patients employing techniques similar to those described, except that pretreatment with dipyridamole was omitted. Hemodynamic effects similar to those described above were observed at adenosine dosages of 0.2–0.35 mg per kg per minute. The enhanced cardiac output obtained with adenosine, in combination with the maintained right and left heart filling pressures, is in contrast with the hemodynamic effects of controlled hypotension with sodium nitroprusside or nitroglycerine, as is shown in Table IV.

TABLE IV

Hemodynamic Effects of Adenosine and Nitroglycerine-(TNG), and Nitroprusside-(SNP) Induced Controlled Hypotension during Cerebral Aneurysm Surgery with Similar Anesthetic Techniques (Data Presented as Per Cent from Control)

|  | ADENOSINE n = 10 | SNP** n = 17 | TNG*** n = 20 |
|---|---|---|---|
| MABP | −43* | −36* | −36* |
| RAP | +6 | −39* | −45* |
| PAP | +15 | −27* | −34* |
| PCWP | +14 | −44* | −45* |
| HR | +9* | +22* | +19* |
| QT | +44* | −15* | −24* |
| SVR | −61* | −29* | −16* |
| PVR | −15 | +11 | +12 |

*$p < 0.01$
**Data from Lagerkranser et al., Acta. Anesth. Scand., 24: 426–32 (1980).
***Data from Lagerkranser, Acta. Anesth. Scand., 26: 453–7 (1982).

From the foregoing it is evident that continuous infusion of adenosine during anesthesia is capable of significantly reducing blood pressure without evidence of tachyphylaxis while, at the same time, causing a decrease in peripheral vascular resistance, an increase in cardiac output and a moderate increase in heart rate. This suggests that adenosine acts as a hypotensive agent through dilation of the arterial resistance vasculature. In contrast, sodium nitroprusside and nitroglycerine induce hypotension by both pre- and post-capillary dilatation. In addition, controlled hypotension with adenosine better preserves oxygen tissue pressures than hypotension induced by nitroprusside.

It should be noted that, at the levels of adenosine used, blockage of atrio-ventricular conductance does not occur in these persons during anesthesia. Indeed, adenosine is used in bolus form specifically to block A-V conductance. Apparently the peak plasma concentration of adenosine is considerably higher when giving bolus injections than the steady state levels obtained during these continuous infusions.

EXAMPLE II

Control of Hypertensive Crisis

Continuous infusion of adenosine can also be employed to control hypertensive crises occurring during surgery. Such crises can occur, for example, as a result of release of catecholamines during surgery on pheochromocytoma—a tumor characterized by the presence of catecholamine—which can cause pulmonary edema and death. At present, this situation is treated prophylactically by pre-administration of alpha- and beta-adrenoceptor blockers or vasodilators, but the effect is often insufficient. It has now been found that, in the case of a catecholamine-induced hypertensive crises, prompt infusion of adenosine will rapidly restore blood pressure to normal, and will easily maintain normal pressure until the crisis has passed. Amounts of adenosine which are effective in controlling such hypertensive crises will depend on the degree of hypertension. However, as a general rule they are about half of the amounts found useful for controlled hypotension, i.e., in the range of from about 0.1 to about 0.2 mg adenosine per kilogram of body weight per minute.

EXAMPLE III

Improved Coronary Circulation in Ischemic Heart Disease

Patients requiring abdominal vascular surgery, such as surgery for an aortic aneurysm, frequently also suffer from ischemic heart disease, or insufficient blood flow to the heart tissue, which may present undesirable complications in such surgery. Accordingly, drugs with vasodilator properties, such as isoflurane and nitroprusside, have been investigated for possible use to increase myocardial blood flow and to reduce peripheral vascular resistance (after-load reduction) during such surgery; however, they have been found to have no beneficial effect with respect to coronary flow and, indeed, may reduce coronary blood flow. In contrast, adenosine administered by continuous infusion has been found very effective in increasing myocardial blood flow and, in such use, is accompanied by an increase in cardiac output, For such application, the rate of adenosine administration should be such that there is no more than a 10-20 percent reduction in blood pressure. As a general rule, this is achieved by use of rates of administration of the order of 0.05 to about 0.1 mg. adenosine per kilogram per minute. In such a case myocardial blood flow has been found to be doubled, cardiac output has been increased by 10 to 20 percent, and blood pressure has been reduced by 10 to 20 per cent, all without change in oxygen consumption and without ECG signs of ischemia.

EXAMPLE IV

Coronary Vasodilation

It has been further found that when adenosine is administered by infusion at rates which do not induce significant hypotension, it has clinically useful regional effects in unanesthetized and anesthetized patients.

For example, adenosine at dosages of the order of 10 to 15 percent of hypotensive levels (e.g. 0.02 to 0.05 mg. per kg. per minute) can be a useful adjunct to coronary bypass surgery, apparently due to a preferential coronary vasodilation. It has been reported that corollary artery grafts occlude more frequently during the post-operative period when low graft-flow values are obtained during surgery. See Groudin et al, Circulation, 42: Suppl 3: 106–111 (1970). It has been found that low doses of adenosine administered post-operatively increase graft blood flow without significant effect on atrio-ventricular conductance. The administration of low doses of adenosine for this purpose can be carried out for as long as is necessary to afford appropriate graft flows and reduce risk of occlusion, but ordinarily the period need not exceed 48 hours following surgery.

In a study designed to investigate the use of adenosine to inhibit occlusion of coronary grafts, nine patients (age 45–65, all taking beta-blockers) were studied during coronary artery surgery. After premedication, morphine (10–15 mg) and scopolamine (0.4–0.6 mg), anesthesia was induced by fentanyl (30 mcg/kg.b.w.). Pancuronium (0.1 mg/kg b.w.) was given to facilitate endotracheal intubation. Anesthesia was maintained with fentanyl 0.5 mg/hour, $N_2O$ (50%) in oxygen and droperidol (0.1 mg/kg b.w.). During bypass thiomebumal (5 mg/kg b.w.) was given. Nitrous oxide was not used after bypass. Extracorporeal circulation (ECC) was performed with a roller pump and a Shiley bubble oxygenator primed with crystalloid solution. ECG (modified $V_5$), an arterial line and a Swan-Ganz Catheter were used for monitoring and for hemodynamic measurements. Blood flow in bypass grafts (n=15, internal mammary and venous grafts), was measured with appropriate sized square wave electromagnetic flow probes (Nycotron 732). The study was performed 20–30 minutes after the termination of ECC. After a control period (5 min), adenosine (5.3 mg/ml. clinical solution) was continuously infused in a central vein in order to induce approximately 10% reduction of mean arterial blood pressure (about 30 to 50 μg per kg. per min.). Graft flow was continuously measured before and during a 10 or 30 minute infusion of adenosine and finally during the following 5 minute control period. Data are expressed as mean ±SEM and differences were tested with Student's paired t-test against the preceding period.

The results of this study are summarized in Table V.

TABLE V

| | CONTROL BEFORE | ADENOSINE | CONTROL AFTER |
|---|---|---|---|
| Mean Arterial Pressure (mmHg) | 84 ± 3 | 74 ± 3 | 85 ± 3 |
| | | $p < 0.01$ | $p < 0.01$ |
| Heart Rate (beats/min) | 82 ± 5 | 82 ± 15 | 81 ± 6. |
| Cardiac Output (l/min) | 4.8 ± 0.4 | 5.6 ± 0.3 | 5.3 ± 0.3 |
| | | $p < 0.05$ | n.s. |
| Pulmonary Artery Pressure (mean) (mmHg) | 16.7 ± 1.2 | 18.8 ± 1.2 | 19.9 ± 1.0 |
| RAP (mean) (mmHg) | 4.7 ± 0.5 | 5.3 ± 0.4 | 5.8 ± 0.7 |
| Stroke Index (ml/m$^2$) | 35.6 ± 2.6 | 38.8 ± 2.0 | 39.6 ± 2.5 |
| Left Ventricular Stroke Index (Joule/n$^2$) | 0.44 ± 0.03 | 0.41 ± 0.03 | 0.49 ± 0.04 |
| Graft flow ml/min (n = 15) | 40 ± 5 | 77 ± 7 | 39 ± 5 |
| | | $p < 0.001$ | $p < 0.001$ |

As is evident from Table V, adenosine in a dose of ±4 μg/kg/minute, a level which reduced mean arterial pressure 12%, increased cardiac output 12%, and doubled graft flow. At the same time, heart rate, mean pulmonary artery pressure, central venous pressure, stroke index and left ventricular stroke work index remained essentially unchanged. Graft flow rate was restored to its original value on termination of adenosine. No arrhythmias were observed.

This demonstrates that i.v. adenosine at low rates (30–50 μg per kg per min) induces a marked and reproducible increase in graft flow without increased myocardial work, apparently due to preferential vasodilatory effect of adenosine in the coronary vasculature.

EXAMPLE V

Increased Cardiac Output

As is evident from the foregoing data, intravenously infused adenosine has the ability to increase cardiac output without increasing heart work. This is in contrast to other vasodilators, such as sodium nitroprusside, which may reduce cardiac output, depending on the hemodynamic status of the patient. As a consequence, adenosine can be used to stimulate cardiac output in patients with low cardiac output states, due, for example, to heart surgery, infarct and the like. This apparently is due to adenosine's ability to reduce after-load, without having significant effect on pre-load. In contrast, nitroprusside reduces both after-load and pre-load, and nitroglycerine is effective principally (90%) on reducing pre-load, and has only a marginal effect on after-load.

For this application, effective dosages are intermediate those used for increased graft flow and controlled hypotension. Typically the effective dose is of the order of 40–80 μg/kg/per minute. The duration of treatment can be as long as required to support the heart. It also has been found that, on termination of the adenosine, cardiac output, although less than that during treatment with adenosine, frequently remains above the cardiac output prior to treatment.

In this respect, adenosine is of value as an adjunct to dopamine treatment for cardiogenic shock. Dopamine is frequently given to patients in shock to stimulate heart action and thereby increase blood pressure. Adenosine can be administered with dopamine to modulate peripheral resistance without compromising systemic blood pressure, and thus increase cardiac output.

Adenosine is unique in its activity in this respect, because it is able to reduce after-load without significantly increasing heart rate. In contrast, agents previously used to reduce cardiac after-load, for example, hydralazine and prazosin, increase heart rate.

EXAMPLE VI

Platelet Protection During Cardiopulmonary Bypass

Continuous infusion of adenosine also has been found of use in protecting platelets during cardiopulmonary bypass. For such use, it is desired to maintain the adenosine dosage below that affording significant vasodilation, and a rate of about 100 μg/kg/min has been found effective. In contrast, prostacyclin, a prostaglandin used to inhibit platelet aggregation, is associated with severe systemic vasodilation and hypotension during coronary bypass surgery.

Twenty-five patients scheduled for coronary artery bypass surgery were randomly assigned to two groups—one with adenosine infusion (n=13) and the other with placebo infusion (n=12).

Routine tests of-coagulation status were normal in all patients, and none was taking drugs known to affect platelet function. Intravenous anesthesia was used, either high-dose fentanyl (100–150 μg/kg) or balanced anesthesia (thiopental, fentanyl, diazepam and N$_2$O/O$_2$).

During cardiopulmonary bypass (CPB), mean arterial blood pressure (MABP) above 70 mmHg was treated with the vasodilator sodium nitroprusside (SNP), except in the final phase or rewarming. CPB was performed with SARN roller pump and a Shiley oxygenator (100 A) primed with 2000 ml crystalloid solution (75 mg heparin). The perfusion rate was kept at approximately 1.8 ml/m$^2$ body surface. Moderate hypothermia (25° C.) was induced. Cardioplegia was obtained with Ringer's solution (with added potassium up to 20 mM/l). Heparin (3 mg/kg) was administered as a bolus injection before cannulation. The heparin effect was controlled by measurements of activated clotting time. (Hemocron ® Int. Technidyne Corp, USA). This time (ACT) was >400 seconds in all patients during CPB. At the termination of CPB, the heparin effect was antagonized with protamine (c. 1.3 mg/mg heparin). ACT was checked 10–20 min after the protamine injection. ACT values 120 sec were considered satisfactory.

Platelet count (Linson 431 A cell counter) and hematocrit were determined in arterial samples before anesthesia, after thoracotomy, during CPB at 10, 20, 40, 60, 80 and 100 min, 30 min after CPB and on the postoperative day. Platelet counts were expressed in percentage of preanesthesia levels and were corrected for hemodilution MABP was monitored continuously via a catheter introduced in the radial artery. All patients received hypertonic mannitol (1–1.5 g/kg) during CPB and urine production was calculated as ml/.min of CPB (Table VI).

Peroperative blood loss and blood transfusions could not be compared between the groups, due to the smallness of the series and the involvement of many surgeons in the study. Postoperative bleeding was measured as the blood loss from the tube drainage from the end of operation until the postoperative morning. One patient in the adenosine group was excluded because of reoperation for surgical reasons (for massive bleeding due to suture insufficiency in a graft anastomosis) within 6 hours after CPB.

Adenosine (5.3 mg/ml, clinical solution) was infused at a rate of 100 µg/kg/min into the superior vena cava throughout CPB. The adenosine dose was based on five pilot cases in which a vasodilation dose-response was observed. The highest infusion rate that did not induce systemic vasodilation was chosen for this study. In six cases the plasma adenosine levels were determined by high performance liquid chromatography (HPLC) (Fredholm and Sollevi, J. Physiol. (London), 313: 351–67 (1981) in arterial and in venous (venous lines to the oxygenator) blood. The adenosine metabolites inosine, hypoxanthine and uric acid were also determined by HPLC. The samples were collected as previously described (Sollevi, Acta. Physiol. Scand., 121: 165–72 (1984) at the intervals of 10, 20, 40 and 80 minutes during CPB and 20 minutes after CPB.

Results are summarized in Tables VI and VII, below, in which data are presented as means ±SEM. Statistical significance (controls v. adenosine group) was determinted with Student's t-test for unpaired data. For significance within the groups the Wilcoxon Rank Sum test was used. $p<0.05$ was regarded as significant.

TABLE VI

| PATIENT DATA | | |
|---|---|---|
| | Adenosine (mg per kg per min) | |
| | 0 | 0.1 |
| Age, years | 57 (range 47–66) | 57 (range 42–74) |
| Males/females | 11/1 | 12/1 |
| CPB-time (min) | 95 ± 10 | 120 ± 10 |
| Preoperative platelet counts (× 10$^9$ cells/l) | 162 (range 107–235) | 158 (range 106–251) |
| Peroperative urine production (ml/min CPB) | 9.7 (2.1–20) | 4.1 (1.1–9.5) |
| Postoperative blood loss (ml) | 630 ± 60 | 640 80 |

TABLE VIII

| | Platelet Count; % of Awake Count | |
|---|---|---|
| Time of count | Control | Adenosine |
| Awake | 100 | 100 |
| Pre CPB | 95 | 97 |
| During CPB (Duration 100 minutes) | | |
| 10 minutes | 80 | 96 |
| 20 minutes | 75 | 87 |
| 40 minutes | 65 | 85 |
| 60 minutes | 80 | 91 |
| 80 minutes | 78 | 100 |
| 100 minutes | 77 | 97 |
| Post CPB, time after infusion of CPB | | |
| 30 minutes | 70 | 88 |
| 24 hours | 60 | 60 |

As shown in Table VIII, platelet count was similar in the two groups before anesthesia and was unaltered by anesthesia and thoracotomy. In the control group the platelet count fell rapidly and markedly during the first 40 minutes of CPB and remained significantly reduced during and after CPB. During adenosine infusion the initial platelet reduction was small, and was significant only at 20 and 40 minutes on CPB. From 60 minutes to the end of CPB and at 30 minutes after CPB the platelet counts were not significantly different from those before anesthesia. Throughout CPB and 30 minutes after CPB there was significant intergroup difference in platelet counts. On the day after operation the platelet counts were markedly reduced in both groups, with no significant intergroup difference.

As shown in Table VII, the arterial and venous adenosine levels were in the normal range of 0.3 µM prior to CPB. The adenosine infusion raised the venous plasma concentration to 2–10 µM, while the arterial levels were approximately doubled during the initial CPB period. Only the first adenosine metabolite, inosine, was consistently elevated during the infusion.

All parameters had returned to control levels within 20 minutes after CPB.

The mean arterial blood pressure (MABP) did not differ significantly between the two groups during CPB. In the placebo group, however, seven patients required sodium nitroprusside infusion ($<5$ µg/kg/min) to keep MABP below 70 mmHg. No patient in the adenosine group required vasodilator treatment. After CPB the patients in the adenosine group had slightly lower MABP, but at the end of operation there was no intergroup difference. The urine production during CPB was 250 ml/h in the adenosine group and 500 ml/h in the controls ($p<0.01$, Table VI). Tran-

TABLE VII

Arterial and Venous Concentrations (µM) of Adenosine and its Metabolites (n = 6), Before, During and After Adenosine Infusion (0.1 mg × kg-1 × min-1)

| | pre-CBP | CPB | | | | CPB 20' post |
|---|---|---|---|---|---|---|
| | | 10' | 20' | 40' | 80' | |
| Vein Adenosine | 0.3 ± 0.2 | 3.7 ± 1.3* | 5.7 ± 2.1* | 4.5 ± 1.1* | 3.0 ± 1.0* | 0.4 ± 0.1 |
| Inosine | 0.2 ± 0.1 | 0.9 ± 0.3* | 2.4 ± 1.2* | 1.6 ± 0.5* | 1.6 ± 0.4* | 0.4 ± 0.1 |
| Artery Adenosine | 0.3 ± 0.1 | 0.7 ± 0.3 | 0.8 ± 0.4* | 0.6 ± 0.3 | 0.4 ± 0.2 | 0.3 ± 0.1 |
| Inosine | 0.2 ± 0.1 | 1.3 ± 0.7* | 2.5 ± 1.0* | 1.2 ± 0.3* | 1.4 ± 0.4* | 0.4 ± 0.1 |
| Hypoxanthine | 3.2 ± 0.8 | 5.3 ± 1.2 | 7.7 ± 1.4* | 5.3 ± 1.0 | 5.0 ± 0.9 | 4.2 ± 0.9 |
| Uric Acid | 250 ± 30 | 260 ± 32 | 269 ± 35 | 250 ± 32 | 249 ± 30 | 260 ± 34 |

*Significantly different from pre-CPB value.

sient elevation of serum creatinine levels (10–20% above normal range) was found in two patients in the adenosine group and one control patient during two postoperative days. The postoperative blood loss did not differ between the groups.

All patients were extubated within 24 hours after the operation and all recovered normally. There were no clinical signs of neurologic complications and all the patients were discharged from the hospital.

EXAMPLE VII

Addition of Adenosine to Cardioplegia Solution

Cardioplegia is induced during open heart surgery in order to arrest the heart and to reduce myocardial oxygen consumption during cardiopulmonary bypass. This is at present generally obtained by ice-cooled solution containing high concentration of potassium (20 mmol/liter, four times the normal serum level) that is infused into the coronary vessels. It is well known that high concentrations of potassium effectively induce asystole, but also cause damage on vascular endothelium. The latter may lead to permanent stenosis of cornonary vessels.

The foregoing data has clearly demonstrated in human patients that adenosine is effective as coronary vasodilator and preserves circulating platelets. Adenosine is also known to be incorporated into high energy phosphates (ATP) in various tissues. In addition, it is well known since the early work of Drury and SZent Gyorgyi (J. Physiol (London) 68:213 (1929)) that high concentration of adenosine can produce heart block.

These four effects of adenosine are all useful during the induction of cardioplegia in human patients. First, the vasodilatory effect can counteract the vasoconstrictor effect of potassium and thereby reduce the time required for administration of cardioplegia solution. This will give a more rapid cooling and thereby more rapid asystoli. Secondly, the inhibitory effect of adenosine on platelet activation can prevent platelet aggregation in the coronary circulation during this cooling phase. Third, adenosine can serve as a substrate and be incorporated into myocardial ATP during this condition, when the heart is beating without obtaining adequate oxygen supply. Finally, the well known A-V blocking effect of high concentrations of adenosine can be used for the induction of asystoli. Then, the potassium concentration of the cardioplegia solution can be reduced to a level that do not damage the vascular endothelium.

These four effects of adenosine can all be achieved with a cardioplegia solution containing 0.5–1.5 mg/ml of adenosine, administered into the coronary circulation during the induction of cardioplegia. Ordinarily, when adenosine is administered for this purpose through the aortic root, the cardioplegia solution will be administered at the rate of 50 to 150 ml./min. over a period of about 10 to about 20 minutes

EXAMPLE VIII

Decreasing Acute Pulmonary Vascular Resistance

Increased pulmonary resistance, e.g., pulmonary hypertension may clinically manifest as a severe disturbance of myocardial function of the right ventricle, a myocardial insufficency, and an impaired whole body oxygenation. Increased pulmonary resistance may be chronic or acute, ie., occur as a consequence of surgery, or pulmonary disease. The present invention is also directed to decreasing or normalizing acute pulmonary vascular resistance and pulmonary hypertension.

Pharmacological treatment of increased pulmonary vascular resistance or acute pulmonary hypertension has focused on using traditional vasodilating agents. These agents have been shown to have limited effects on pulmonary hypertension. The vasodilatory and hypotensive effects of these agents are primarily systemic, not localized in the pulmonary vasculature.

The endogenous vasodilator adenosine, in contrast to these traditional agents, has been shown to be most effective as a dilator of blood vessels in the organs in animal models as well as in humans. In animal and clinical studies, systemic vasodilator doses of adenosine have had negligible or at most, minor effect on normal pulmonary vascular resistance. Surprisingly, however, in animal models (pig) where pulmonary hypertension has been induced by hypoxic ventilation during anesthesia, intravenous adenosine administration unexpectedly produces a marked reduction in this higher-than-normal pulmonary vascular resistance. Even more surprising is the fact that this decrease in pulmonary vascular resistance occurs at a dosage of adenosine lower than that which exhibits systemic vasodilator effects. This effect is obtained at doses of adenosine that commonly do not result in detectable vasodilator effects or effects on cardiac output or arterial oxygen function.

It is believed that adenosine can exert its vasodilatory hypotensive effects in the pulmonary circulation without inducing systemic vasodilation because of its extremely rapid elimination in the blood stream (T1/2 less than 10 seconds). Thus, a dose titration of adenosine can be performed, producing effects in the pulmonary vasculature without producing systemic effects at least in part because the adenosine is eliminated before it reaches the resistance vessels of the systemic vasculature.

The expected suitable infusion rate of adenosine in humans to normalize pulmonary vascular resistance is typically 10–30 micrograms per kilogram of body weight (0.010–0.030 mg. per kg. per minute). As a general rule, the concentration of the adenosine in the infusion solution is at least about 5 millimol (1.5 mg/ml) and may be as high as the solubility limit of adenosine (about 20 millimol or 5.5–6 mg/ml). However, in small children, the concentration of adenosine in solution may be as low as 0.1 mg/ml.

Preferably, to effectuate the maximum pulmonary hypotensive effect, the adenosine solution is administered by infusion through a catheter to maximize the exposure of the pulmonary vasculature to adenosine. This is done by infusing the adenosive solution into a central vein such as the superior vena cava, or alternatively, into the right atrium. As the adenosine solution is infused, the pulmonary vascular resistance is monitored to determine the effect of the adenosine. Infusion of adenosine is maintained until pulmonary vascular resistance returns to normal levels or until there is no further evidence of decreasing pulmonary vascular resistance. Adenosine infusion may, of course, be continued for periods of time within practical limits in particularly difficult cases of higher-than-normal pulmonary vascular resistance. Using this selective pulmonary effect of adenosine, low infusion rates may be used for the treatment of acute postoperative pulmonary hypertension that occurs in patients after heart transplant surgery or in other surgeries.

EXAMPLE IX

Decreasing Pulmonary Vascular Resistance in Conjunction with Idiopathic Respiratory Distress Syndrome Adenosine infusion as described in example VIII may also be used to normalize pulmonary vascular resistance (pulmonary hypertension) in children with idiopathic respiratory distress syndrome (IRDS).

Such treatment may be performed by infusing the low doses of adenosine as described in example VIII into the patient's pulmonary vasculature, e.g. via catheter introduced in the pulmonary artery for a period sufficient to lower pulmonary vascular resistance. The catheter's position should be distal to the ductus arteriosus. This way, adenosine does not enter the systemic circulation. Preferably, pulmonary vascular resistance should be lowered to within normal ranges. Thus, adenosine infusion should be maintained for a period sufficient to normalize pulmonary vascular resistance. This can be done by monitoring pulmonary vascular resistance during the infusion process, and maintaining infusion until pulmonary vascular resistance levels fall to normal. In difficult cases adenosine infusion may be maintained for periods of time within practical limits.

EXAMPLE X

A Method of Diagnosing the Operability of the Pulmonary Vasculature in Patients Exhibiting Pulmonary Hypertension in Conjunction with Cardiac Septum Defects In children with myocardial septum defects (Vitium Organicum Cordis, VOC), who also exhibit pulmonary hypertension, adenosine infusion provides a means by which the value of surgically repairing septum defects can be determined. Adenosine induced reduction of pulmonary vasculature resistance may be a rapid and simplified technique for the evaluation of the usefulness of surgical repair of septum defects. This technique is a welcome diagnostic tool since patients with septum defects having severe morphological damage of the pulmonary vasculature caused by pulmonary hypertension would not normally be responsive to adenosine vasodilation. This condition is not improved by surgical repair of the VOC.

The methodology comprises infusing an adenosine solution (infusion rate of 0.010–0.030 mg. per kg. per minute with a concentration of about 1.5 mg./ml. to about 5.5–6.0 mg./ml.) into the blood stream of a patient to maximize the exposure of the patient's pulmonary vasculature to adenosine. This can be done by infusing a solution of adenosine into a central vein, for example, the superior vena cava, or alternatively, into the right atrium. The blood pressure in the lung artery is then measured before and after administration of the adenosine as per the previously described technique in examples I and VI (cannula introduced in the artery). A decrease of arterial blood pressure is indicative of a reduction of the pulmonary vascular resistance and this, in turn, is an indication that the pulmonary vasculature will respond to surgical repair of the VOC. On the other hand, if there is no decrease in arterial pressure, then this would be indicative of morphological damage of the type that would not be improved by surgery.

An alternative to measuring a decrease in mean arterial pressure is to measure heart minute volume. In this technique, the heart minute volume is measured (same technique as described above in Example I) during administration of adenosine for a time period long enough to observe the pressure or flow change in heart volume. An increase in heart minute volume would indicate that the operability of the pulmonary vasculature had not been impaired, and that the cardiac septum defects could be corrected with surgery. No change would indicate the septum defects could not be corrected with surgery.

EXAMPLE XI

Adenosine in Percutaneous Transluminal Coronary Angioplasty

A new method of treating coronary artery disease in human beings is effected by inserting a special catheter, equipped with an inflatable balloon, into a coronary artery which has an angiographically demonstrable stenosis. The procedure, known as percutaneous transluminal coronary angioplasty (PTCA), is executed as follows: under radiological control, the balloon of the catheter is placed in the stenosed part of the vessel. The balloon is inflated several times, each time with Increasing pressures, and for a duration of 1 minute. Thereafter, the catheter is withdrawn from coronary circulation and the flow through the so treated vessel is checked by means of coronary agniography. The resultant widening of the diseased part of the coronary vessel leads to cracks in the intimal cell layer of the vessel. This trauma leads to activation of biochemical processes leading to local production of substances able to constrict the vessel, as well as activating platelets, which are circulating in the blood, in such a way that they are more easily deposited on the site of the previous stenosis. Such a platelet deposition is the first initiation of the coagulation process, which ultimately can lead to the formation of a blood clot. All these events act in conjunction to counter the intended effect of the PTCA treatment, and may ultimately lead to a re-occlusion of the vessel. During the period the PTCA procedure has been in widespread use, re-occlusions have been found to occur within 6 months of treatment in 25% or more of the cases. It is generally agreed that 5–10% or more occur in the first few days after treatment.

In order to lessen or prevent the negative effects of PTCA described above, vasodilating substances such as nitroglycerine, sodium nitroprusside, and the like, as well as platelet inhibiting substances and substances preventing blood coagulation such as acetylsalicylic acid, dipyridamol, heparin, coumarin and warfarin, have been administered to the patient before and after the procedure. However, all these substances have actions that are either too potent to be safe in conjunction with the PTCA procedure, since bleeding complications from the catheter puncture sites may occur, or too weak or unpredictable to be fully effective.

Adenosine may be used effectively in conjunction with PTCA because it possesses a unique combination of beneficial properties which all work to antagonize the complicating reactions described above. It has a potent vasodilatory effect on the coronary circulation which enables good blood flow through the treated vessel, which in turn prevents platelet deposition on the traumatized vessel site. In addition, adenosine antagonizes the action of locally produced vaso-constrictor substances. Adenosine also has an inhibiting effect on platelet aggregation, which further inhibits the chances of clot formation in the treated vessel. These effects are further enhanced by the ability of adenosine to inhibit presynaptic neural mechanisms regulating the release of catecholamines from nerve endings of the sympathetic nervous system which, as is well known, have consequences that all work for clot formation.

The adenosine dosage anticipated to be effective in this context is typically from 10 to 100 microgram of adenosine per kilogram per minute. Since the PTCA procedure is performed in an awake patient, higher doses will generally not be employed, since such doses produce symptoms such as facial flushing, neck and chest oppression, palpitation and increased rate of respiration in an awake patient which, although not harmful or life-threatening, nonetheless should be avoided because they may induce anxiety.

Adenosine is preferably administered into a peripheral vein such as the femoral vein or brachial vein. Preferably, administration is begun shortly, e.g., a few minutes, before PTCA and continued for the duration of the PTCA and for several hours, e.g., 24 hours after PTCA.

The adenosine treatment may be given to patients undergoing the PTCA treatment under current medication with other anti-anginal drugs, such as adrenergic blocking drugs, calcium antagonists, diuretics, digitalis glycosides, angiotension converting enzyme inhibitors, antihyperlipidemic drugs, nitrate compounds including nitroglycerin or other vasodilatory compounds.

EXAMPLE XII

Adenosine in Coronary Thrombolysis

A recent advance in the treatment of acute myocardial infarction is by means of introducing substances in the bloodstream to dissolve the clot(s) in the coronary circulation, which in most cases are the cause of the diseased state. This procedure, which is generally referred to as coronary thrombolysis (CTL), is performed by introducing streptokinase, urokinase or tissue plasminogen activator, either intravenously or directly into the coronary circulation. All of the advantages noted above for use of adenosine in PTCA are also applicable to the CTL procedures now in use, or which may be used in the future, since the same vascular and platelet reactions which occur with PTCA also occur in CTL once the thrombolysis has been achieved. In the CTL context, however, it may be advantageous to administer the adenosine concomitantly with the thrombolytic agent, either separately or premixed with it in a fixed solution, such premixed solution being a further aspect of this invention. When the two agents are administered separately, it is desirable but not essential that the initiation of administration of each be simultaneous. For example, administration of the adenosine may be initiated before administration of the thrombolytic agent.

IN CTL, as in PTCA, adenosine may be administered intravenously at the same dosage as with PTCA. It is recognized that, due to the very brief half-life of adenosine, the dose is dependent on the site of administration. For example, a 30-microgram dose of adenosine per kilogram per minute given in the right atrium of the heart provides very similar effects to a 50-microgram dose of adenosine per kilogram per minute given in a forearm vein. It is conceivable that in CTL procedures, adenosine may be given directly in the coronary circulation. The dose then needed to achieve the same effects as described with intravenous administration would then be expected to lie in the range of 5 to 30 microgram of adenosine per kilogram per minute.

EXAMPLE XIII

Adenosine in the Diagnosis of Coronary Heart Disease by Radionucleide Scintigraphy In the diagnosis of coronary heart disease, modern techniques include visualization of myocardial irrigation by means of injecting short-lived radio-isotopes, such as thallium-201, into the blood-stream and record, by means of a gamma-radiation detector, the activity over the heart muscle.

It has been shown that an injection of the vasodilator dipyridamole can augment the redistribution of flow within the heart muscle so that those areas irrigated by stenosed vessels may be better visualized. The mechanism behind this is the so-called "steal" phenomenon: with a generalized maximal vaso-dilation of the heart muscle, relatively more blood will flow through the vessels not stenosed or constricted in any other way, thereby "stealing" the flow from the area supplied through a stenosed vessel.

Dipryridamol is an adenosine uptake inhibitor, which means it prevents adenosine from crossing the cell-/membranes of the red blood cells from the plasma to the interior (the normal, rapid main pathway for adenosine elimination from plasma), thereby increasing the adenosine levels in plasma. Most data concerning the mechanism of action of dipyridamole's vasodilatory effect in fact support the view that it is solely due to adenosine vasodilation.

In a further aspect of this invention, adenosine can be used instead of dipyridamole in the diagnostic test described. It would in fact be an advantage to use adenosine insofar as it can be dosed exactly and dose-titrated to a precise effect, whereas with dipyridamole, the adenosine levels are unpredictable. Thus, a safer and more reliable test can be expected if adenosine is used.

The exact dose will normally have to be titrated individually but should lie in the range of 10 to 150 micrograms per kilogram per minute.

This invention has been described in terms of specific embodiments set forth in detail herein, but it is to be understood that these are by way of illustration and the invention is not necessarily limited thereto. Modifications and variations will be apparent from the disclosure and may be resorted to without departing from the spirit of the invention as those of skill in the art will readily understand. Accordingly, such variations and modifications are considered to be within the purview and scope of the invention and the following claims.

What is claimed is:

1. In a method for percutaneous transluminal angioplasty (PTCA), for treating coronary artery disease in a human patient comprising inserting a catheter having an inflatable balloon into a coronary artery which has an angiographically demonstrable stenosis, and inflating the balloon, the improvement of administering adenosine to said patient by continuous intravenous infusion to lessen negative effects of said PTCA.

2. A method as claimed in claim 1 wherein adenosine is infused into a peripheral vein.

3. A method as claimed in claim 1 wherein administration of adenosine is begun shortly before the PTCA procedure and continued during and several hours after said procedure.

* * * * *